United States Patent

Manero et al.

[11] Patent Number: 5,888,422
[45] Date of Patent: Mar. 30, 1999

[54] FLUORINATED PHENANTHRENE DERIVATIVES AND THEIR USE IN LIQUID-CRYSTAL MIXTURES

[75] Inventors: Javier Manero, Frankfurt; Rainer Wingen, Hattersheim, both of Germany

[73] Assignee: Hoechst Aktiengesellschaft, Frankfurt, Germany

[21] Appl. No.: 983,076

[22] PCT Filed: Jun. 19, 1996

[86] PCT No.: PCT/EP96/02653

§ 371 Date: Dec. 31, 1997

§ 102(e) Date: Dec. 31, 1997

[87] PCT Pub. No.: WO97/02247

PCT Pub. Date: Jan. 23, 1997

[30] Foreign Application Priority Data

Jul. 4, 1995 [DE] Germany ............ 195 24 230

[51] Int. Cl.⁶ .......... C09K 19/32; C07D 22/10; C07D 47/02; C07C 23/44
[52] U.S. Cl. .......... 252/294.62; 544/345; 544/347; 546/101; 546/108; 570/183; 570/129
[58] Field of Search ......... 252/299.62; 544/345, 544/347; 546/81, 82, 88, 101, 108; 570/129, 183; 428/1

[56] References Cited

U.S. PATENT DOCUMENTS

| | | | |
|---|---|---|---|
| 4,421,670 | 12/1983 | Deutscher et al. | 252/299.62 |
| 5,075,032 | 12/1991 | Hopf et al. | 252/299.63 |
| 5,648,021 | 7/1997 | Wingen et al. | 252/299.62 |

FOREIGN PATENT DOCUMENTS

| | | |
|---|---|---|
| 2243925 | 4/1975 | France . |
| 2490233 | 3/1982 | France . |
| 4402986 A1 | 8/1995 | Germany . |
| 19500768 A1 | 9/1995 | Germany . |
| WO 87/01717 | 3/1987 | WIPO . |
| WO 95/21227 | 8/1995 | WIPO . |

OTHER PUBLICATIONS

Caplus 1967:85634, 1967.
Caplus 1976: 4720, 1976
Caplus 1976: 59025, 1976.
Caplus 1976: 135361, 1976.

*Primary Examiner*—Shean O. Wu
*Attorney, Agent, or Firm*—Frommer Lawrence & Haug LLP

[57] ABSTRACT

Fluorinated phenanthrene derivatives of the formula (I)

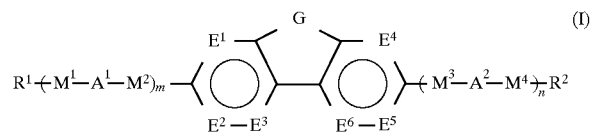

in which the symbols and indices have the following meanings:

$E^1$, $E^2$, $E^3$, $E^4$, $E^5$ and $E^6$ are identical or different and are —N—, —CF— or —CH—;

G is —$CF_2CF_2$— or —CF=CF—;

$R^1$ and $R^2$ are, for example, alkyl or alkoxy;

$M^1$, $M^2$, $M^3$ and $M^4$ are, for example, O, —CO—O—, —O—CO— or a single bond;

$A^1$ and $A^2$ are, for example, 1,4-phenylene or pyrimidine-2,5-diyl;

m and n are zero or one, but in total are not more than one, are suitable as components of liquid-crystalline mixtures.

9 Claims, No Drawings

FLUORINATED PHENANTHRENE DERIVATIVES AND THEIR USE IN LIQUID-CRYSTAL MIXTURES

This application is a 371 of PCT/EP96/02653 filed Jun. 16, 1996.

In addition to nematic and cholesteric liquid crystals, recent times have also seen the use of optically active tilted smectic (ferroelectric) liquid crystals in commercial display devices.

Clark and Lagerwall showed that the use of ferroelectric liquid crystals (FLCs) in very thin cells leads to optoelectric switching or display elements having response times faster by a factor of up to 1000 than those of the conventional TN (twisted nematic) cells (see, for example, EP-A 0 032 362). On the basis of these and other favorable properties, for example the possibility of bistable switching and the contrast, which is virtually independent of viewing angle, FLCs are in principle highly suited to applications such as computer displays.

For the use of FLCs in electrooptical or completely optical assemblies there is a need either for compounds which form tilted or orthogonal smectic phases and which are themselves optically active, or else for compounds which, although forming such smectic phases are not themselves optically active, can be doped with optically active compounds to induce ferroelectric smectic phases. The desired phase should at the same time be stable over as wide as possible a temperature range.

Obtaining a good contrast ratio in electrooptical assemblies necessitates a uniform planar orientation of the liquid crystals. Good orientation in the $S_A$ and $S^*_c$ phase can be achieved, for example, when the phase sequence of the liquid-crystal mixture with decreasing temperature is as follows:

isotropic→$N^*$→$S_A$→$S^*_C$

A precondition is that the pitch of the helix in the $N^*$ phase is very large (greater than 10 μm) or, even better, is fully compensated (see, for example, T. Matsumoto et al., p.468–470, Proc. of the 6th lnt. Display Research Conf., Japan Display, Sep. 30–Oct. 2, 1986, Tokyo, Japan; M. Murakami et al., ibid. p. 344–p. 347). This is done, for example, by adding one or more optically active dopes which induce, say, a right-handed helix to the chiral liquid-crystal mixture which in the $N^*$ phase has a left-handed helix, in amounts such that the helix is compensated.

For the use of the SSFLCD effect (Surface Stabilized Ferroelectric Liquid Crystal Display) of Clark and Lagerwall for uniform planar orientation a further precondition is that the pitch in the smectic $C^*$ phase is substantially greater than the thickness of the display element (Mol. Cryst. Liq. Cryst. 1983, 94, 213 and 1984, 114, 151). This can be done, as in the case of the cholesteric pitch, by using dopes with the opposite helical rotation.

The optical response time τ[μs] of ferroelectric liquid-crystal systems, which should be as short as possible, depends on the rotational viscosity of the system γ[mPas], on the spontaneous polarization $P_s$[nC/cm$^2$] and on the electric field strength E[V/m] in accordance with the relationship

$$\tau \sim \frac{\gamma}{P_s \cdot E}$$

Since the field strength E is determined by the electrode separation in the electrooptical component and by the applied voltage, the ferroelectric display medium must be of low viscosity and must have a high spontaneous polarization in order for a short response time to be obtained. Finally, requirements in addition to thermal, chemical and photochemical stability are for a small optical anisotropy Δn, preferably≈0.13, and a small positive or, preferably, negative dielectric anisotropy Δε (see, for example, S. T. Lagerwall et al., "Ferroelectric Liquid Crystals for Displays", SID Symposium, October Meeting 1985, San Diego, Calif., USA). The entirety of these requirements can only be met with mixtures of two or more components. The basis of these mixtures (or matrix) is preferably formed by compounds which as far as possible themselves already have the desired phase sequence I→N→$S_A$→$S_C$. Further components are often added to the mixture in order to lower the melting point and to broaden the $S_C$ phase and usually the N phase as well, for inducing the optical activity, for pitch compensation and for adapting the optical and dielectric anisotropy, as far as possible without increasing the rotational viscosity, for example.

Ferroelectric liquid-crystal displays can also be operated by utilizing the DHF (Distorted Helix Formation) effect or the PSFLCD (Pitch Stabilized Ferroelectric Liquid Crystal Display, also called SBF=Short Pitch Bistable Ferroelectric) effect. The DHF effect was described by B. I. Ostrovski in Advances in Liquid Crystal Research and Applications, Oxford/Budapest 1980, 469 and the PSFLCD effect is described in DE-A 39 20 625 and EP-A 0 405 346. In contrast to the SSFLCD effect, utilizing these effects requires a liquid-crystalline material with a short $S_C$ pitch.

Derivatives of phenanthrene (which here also includes 9,10-dihydro-phenanthrenes) have already been described as liquid crystals or as components of liquid-crystalline mixtures:

Azomethines having a phenanthrene or 9,10-dihydrophenanthrene unit J. Chem. Soc. [London] 1958, 552; J. Chem. Soc., Perkin II 1982, 465); keto derivatives of 9,10-dihydrophenanthrene or phenanthrene (Chem. Ind. [London] 1974, 615 Prod Int. Liq. Cryst. Conf. 1973, 397; Tetrahedron 1981, 37, 2815); carboxyl derivatives of 9,10-dihydrophenanthrene (DD-WP 153 826); 2,7-bis(alkyloxy) phenanthrenes (Nippon Kagaku Kaishi 1980, 250).

However, since the development—of ferroelectric liquid-crystal mixtures in particular—can in no way be regarded as complete, the manufacturers of displays are interested in a very wide variety of components for mixtures. One of the reasons for this is that only the interaction of the liquid-crystalline mixtures with the individual components of the display device or of the cells (for example the alignment layer) allows conclusions to be drawn about the quality of the liquid-crystalline mixtures too.

The object of the present invention was therefore to provide new compounds which are suitable in liquid-crystalline mixtures for improving the profile of properties of these mixtures.

It has now been found that 2,7-disubstituted phenanthrene derivatives of the formula (I) are particularly suitable for use in liquid-crystal mixtures.

The invention therefore provides compounds of the formula (I)

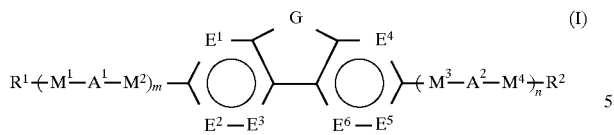

in which the symbols and indices have the following meanings:

$E^1, E^2, E^3, E^4, E^5$ and $E^6$ are identical or different and are —N—, —CF— or —CH—.

Preference is given to compounds of the formula (I) in which $E^1, E^2, E^3, E^4, E^5$ and $E^6$ are identical or different and are —CF— or —CH—.

Particular preference is given to compounds of the formula (I) in which $E^1, E^2, E^3, E^4, E^5$ and $E^6$ are —CH— or in which $E^2, E^3, E^5$ and $E^6$ are —CH— and $E^1$ and $E^4$ are —CF—.

G is —$CF_2CF_2$— or —CF=CF—.

$R^1, R^2$ are identical or different and are hydrogen, —CN, —F, —Cl, —$CF_3$, —$CHF_2$, —$CH_2F$, —$OCF_3$, —$OCHF_2$, —$OCH_2F$ or a straight-chain or branched alkyl radical having 1 to 20 carbon atoms (with or without an asymmetric carbon atom), where alternatively one or more $CH_2$ groups can be replaced by —O—, —S—, —CO—O—, —O—CO—, —O—CO—, —O—CO—O—, —CO—, —CS—, —CH=CH—, —C≡C—, cyclopropane-1,2-diyl, —Si(CH$_3$)$_2$—, 1,4-phenylene, trans-1,4-cyclohexylene or trans-1,3-cyclopentylene, with the proviso that oxygen atoms and/or sulfur atoms must not be attached directly to one another and/or where one or more hydrogen atoms of the alkyl radical can be substituted by —F, —Cl, —Br, —OR$^3$, —SCN, —OCN or —N$_3$, or else are one of the following groups (optically active or racemic):

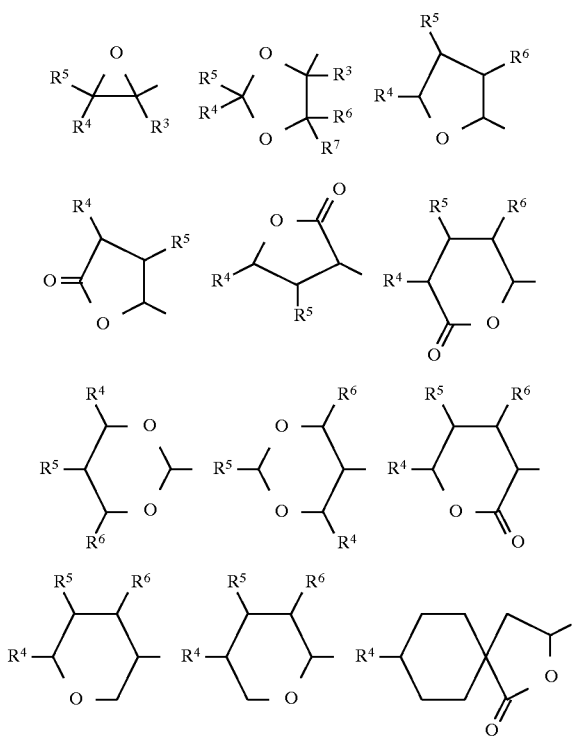

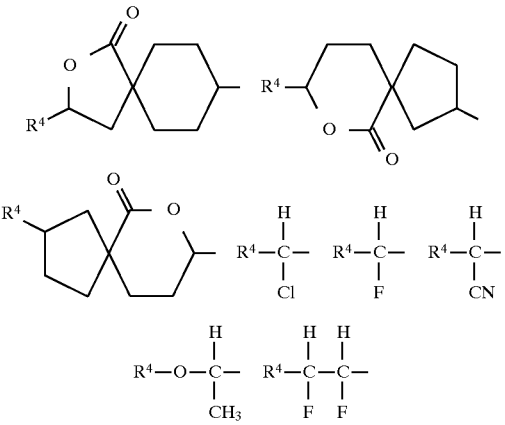

Preferably, $R^1, R^2$ are identical or different and are a straight-chain or branched alkyl radical (with or without an asymmetric carbon atom) having 1 to 16 carbon atoms, where alternatively one or more $CH_2$ groups can be replaced by —O—, cyclopropane-1,2-diyl or —Si(CH$_3$)$_2$—, with the proviso that oxygens must not be directly connected, and/or where one or more hydrogen atoms of the alkyl radical can be substituted by F; $R^1$ or $R^2$ can also be H, but not both simultaneously.

With particular preference, R1, R2 are identical or different and are straight-chain or branched alkyl or alkyloxy radicals having 1 to 10 carbon atoms, where alternatively one $CH_2$ group, separated by at least two further $CH_2$ groups from the nucleus, can be replaced by —Si(CH$_3$)$_2$—.

$R^3, R^4, R^5, R^6, R^7$ are identical or different and are hydrogen or a straight-chain or branched alkyl radical having 1–16 carbon atoms (with or without an asymmetric carbon atom), where alternatively one or more $CH_2$ groups can be replaced by —O— and/or —CH=CH—, with the proviso that oxygen atoms must not be attached directly to one another, and/or where one or more hydrogen atoms of the alkyl radical can be substituted by —F or —Cl; $R^4$ and $R^5$ can together also be —(CH$_2$)$_4$— or —(CH$_2$)$_5$— if they are attached to an oxirane, dioxolane, tetrahydrofuran, tetrahydropyran, butyrolactone or valerolactone system.

$M^1, M^2, M^3, M^4$ are identical or different and are —O—, —S—, —CO—, —CO—O—, —O—CO—, —O—CO—O—, —CO—S—, —S—CO—, —CS—O—, —O—CS—, —S—CS—S—, —O—CS—O—, —S—CO—S—, —CS—, —CH$_2$—O—, —O—CH$_2$—, —CH$_2$—S—, —S—CH$_2$, —CH=CH—, —C≡C—, —CH$_2$—CH$_2$—CO—O—, —O—CO—CH$_2$—CH$_2$— or a single bond.

Preferably, $M^1, M^2, M^3, M^4$ are identical or different and are —O—, —CO—O—, —O—CO—, —O—CO—O—, —CH$_2$—O—, —O—CH$_2$—, —CH=CH—, —C≡C—, —CH$_2$—CH$_2$—CO—O—, —O—CO—CH$_2$—CH$_2$— or a single bond.

With particular preference, $M^1, M^2, M^3, M^4$ are identical or different and are —O—, —CO—O—, —O—CO—, —CH$_2$—O—, —O—CH$_2$— or a single bond.

$A^1, A^2$ are identical or different and are 1,4-phenylene, where one or more hydrogen atoms can be replaced by F, Cl and/or CN, pyrazine-2,5-diyl, where one or two hydrogen atoms can be replaced by F, Cl and/or CN, pyridazine-3,6-diyl, where one or two hydrogen atoms can be replaced by F, Cl and/or CN, pyridine-2,5-diyl, where one or more hydrogen atoms can be replaced by F, Cl and/or CN, pyrimidine-2,5-diyl, where one or two hydrogen atoms can be replaced by F, Cl and/or CN, trans-1,4-cyclohexylene, where one or two hydrogen atoms can be replaced by CN and/or $CH_3$, 1,3,4-thiadiazole-2,5-diyl, 1,3-dioxane-2,5-diyl, 1,3-dithiane-2,5-diyl, 1,3-thiazole-2,4-diyl, where one hydrogen atom can be replaced by F, Cl and/or CN, 1,3-thiazole-2,5-diyl where one hydrogen atom can be replaced by F, Cl and/or CN, thiophene-2,4-diyl, where one hydrogen atom can be replaced by F, Cl and/or CN, thiophene-2,5-diyl where one or two hyrogen atoms can be replaced by F, Cl and/or CN, piperazine-1,4-diyl, piperazine-2,5-diyl, naphthalene-2,6-diyl, where one or more hydrogen atoms can be replaced by F, Cl and/or CN, bicyclo[2.2.2]octane-1,4-diyl, where one or more hydrogen atoms can be replaced by F, Cl and/or CN, or 1,3-dioxaborinane-2,5-diyl.

Preferably, $A^1$, $A^2$ are identical or different and are 1,4-phenylene, where one or more hydrogen atoms can be replaced by F, Cl and/or CN, pyridine-2,5-diyl, where one or more hydrogen atoms can be replaced by F, Cl and/or CN, pyrimidine-2,5-diyl, where one or two hydrogen atoms can be replaced by F, Cl and/or CN, trans-1,4-cyclohexylene, where one or two hydrogen atoms can be replaced by CN and/or $CH_3$, 1,3,4-thiadiazol-2,5-diyl, 1,3-dioxane-2,5-diyl, 1,3-thiazole-2,4-diyl, where one hydrogen atom can be replaced by F, Cl and/or CN, 1,3-thiazole-2,5-diyl, where one hydrogen atom can be replaced by F, Cl and/or CN, thiophene-2,5-diyl, where one or two hydrogen atoms can be replaced by F, Cl and/or CN, or naphthalene-2,6-diyl, where one or more hydrogen atoms can be replaced by F, Cl and/or CN.

With particular preference, $A^1$, $A^2$ are identical or different and are 1,4-phenylene, where one or more hydrogen atoms can be replaced by F, pyridine-2,5-diyl, where one hydrogen atom can be replaced by F, pyrimidine-2,5-diyl, where one hydrogen atom can be replaced by F, trans-1,4-cyclohexylene, where one or two hydrogen atoms can be replaced by CN and/or $CH_3$, or naphthalene-2,6-diyl, where one or more hydrogen atoms can be replaced by F.

n, m are zero or one, but in total not more than 1.

Very particular preference is given to compounds of the formula (Ia) in which $E^1$ and $E^4$ are identical or different and are —CH— and/or —CF— and $E^2$, $E^3$, $E^5$ and $E^6$ are —CH—:

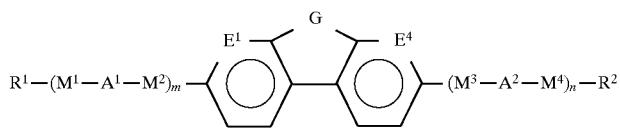

and, of these, especially the compounds

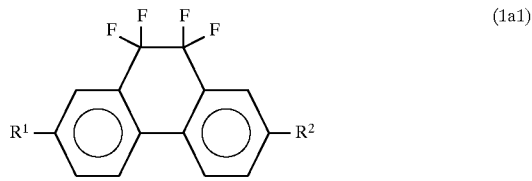

(1a1)

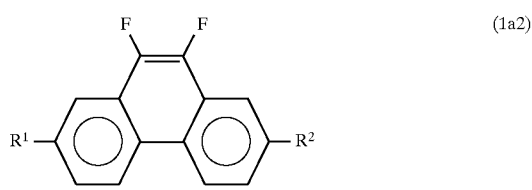

(1a2)

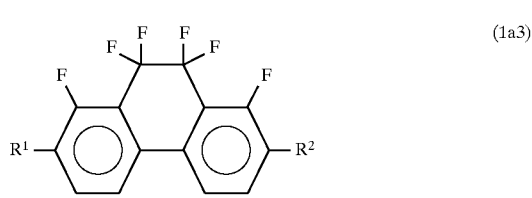

(1a3)

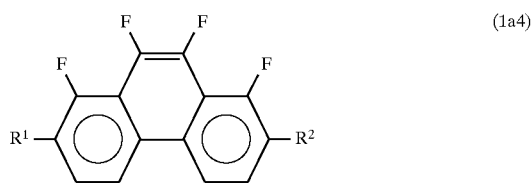

(1a4)

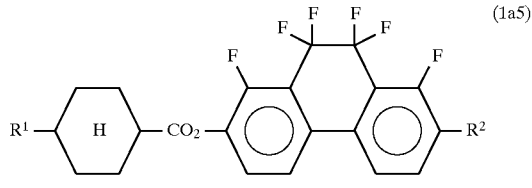

(1a5)

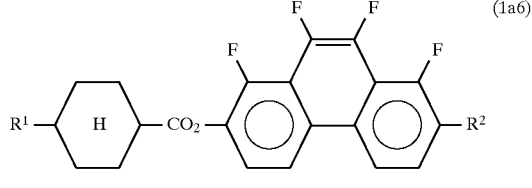

(1a6)

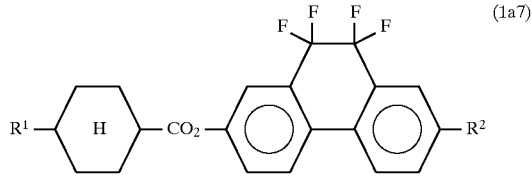

(1a7)

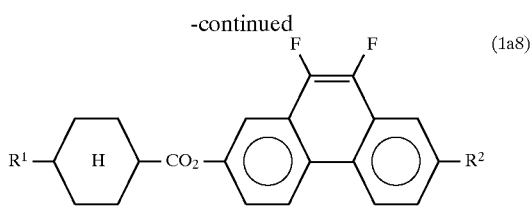

where $R^1$ and $R^2$ have the meanings indicated in the formula (I).

The compounds according to the invention are prepared by methods known per se from the literature, as are described in standard works on organic synthesis, for example Houben-Weyl, Methoden der Organischen Chemie, Georg-Thieme-Verlag, Stuttgart.

The preparation is carried out under reaction conditions which are known and suitable for said reactions. Use may also be made here of variants which are known per se but which are not mentioned here in any more detail.

If desired, the starting materials can also be formed in situ, by not isolating them from the reaction mixture but instead immediately converting them further into the compounds of the formula (I).

By way of example, synthesis routes to compounds of the formula Ia1 and Ia7 or Ia2 and Ia8 are indicated in schemes 1 and 2, although other methods are also conceivable and possible.

Scheme 1:

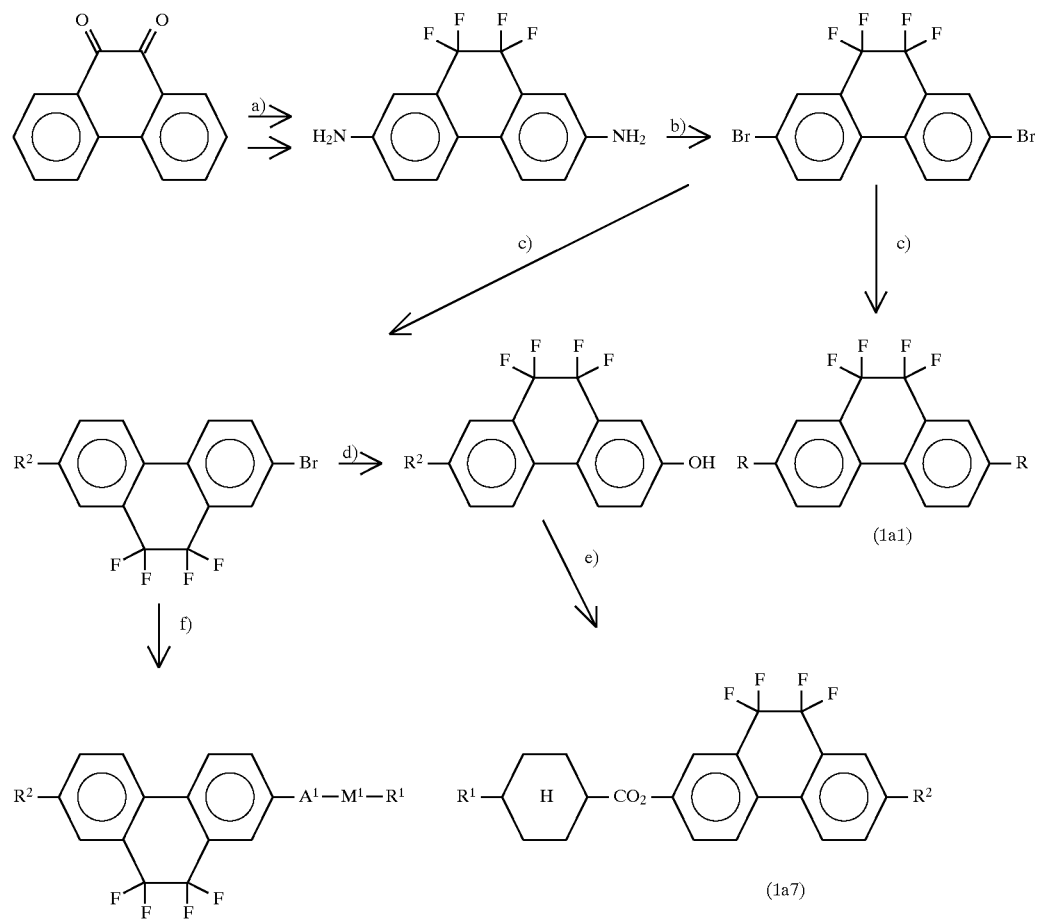

a) Zh. Obshch. Khim 1966, 36, 1815;
b) 1) $NaNO_2$, 2) CuBr; (Sandmeyer reaction);
c) $R^2CuLi$, for overview see Org. Reac, 1975, 22, 253;
d) Glycol/KOH/S; analogous to DE-A 42 36 102;
e) HBTU, analogous to DE-A 44 27 198;
f) analogous to EP-A 0 694 530

Scheme 2:

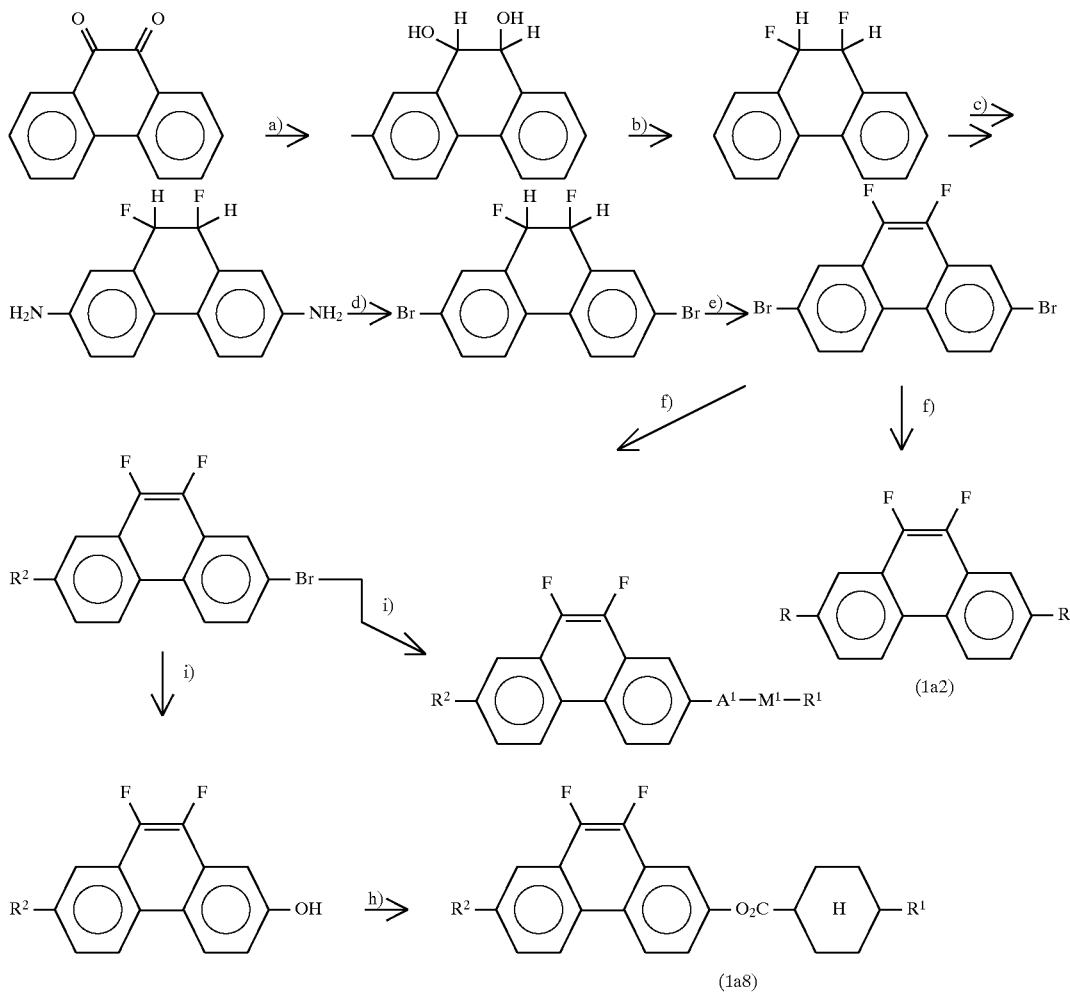

a) LiAlH₄; analogous to JACS 98 (1976) 8114;
b) e.g. Diethylaminosulfur trifluoride (DAST); analogous to J. Org. Chem. 40 (1975) 574;
c) analogous to Zh. Obshch. Khim 1966, 36, 1815;
d) 1. NaNO₂ 2. CuBr (Sandmeyer-reaction);
e) eg. with 2,3-dichloro-5,6-dicyanobenzoquinone; analogous to J.Chem. Soc. 1954, 3569;
f) R²CuLi, overview see Org. Reac. 1975, 22, 253;
g) Glycol, Kolt S, analogous to DE-A42 36 102;
h) HBTU, analogous to DE-A44 27 198;
i) analogous to EP-A-0 694 530

The radical $R^1(-M^1-A^1-M^2)$ or $(-M^3-A^2-M^4)-R^2$ is synthesized by methods which are known per se and are familiar to the skilled worker.

Its preparation takes place under reaction conditions which are known and suitable for said reactions. In this context it is also possible to make use of variants which are known per se and are not mentioned in any more detail here.

Reference may be made, for example, to DE-A 23 44 732, 24 50 088, 24 29 093, 25 02 94, 26 36 684, 27 01 591 and 27 52 975 for compounds with 1,4-cyclohexylene and 1,4-phenylene groups; to DE-A 26 41 724 for compounds with pyrimidine-2,5-diyl groups; to DE-A 40 26 223 and EP-A 03 91 203 for compounds with pyridine-2,5-diyl groups; to DE-A 32 31 462 for compounds with pyridazine-3,6-diyl groups; to EP-A 309 514 for compounds with 1,3,4-thiadiazole-2,5-diyl groups; to WO-A 92/16500 for naphthalene-2,6-diyl groups; to DE-A 37 10 890 for bicyclo[2.2.2]octane-1,4-diyl groups; and to K. Seto et al., Journal of the Chemical Society, Chemical Communications 1988, 56 for dioxaborinane-2,5-diyl groups.

The preparation of disubstituted pyridines, disubstituted pyrazines, disubstituted pyrimidines and disubstituted pyradazines is also given, for example, in the corresponding volumes of the series "The Chemistry of Heterocyclic Compounds" by A. Weissberger and E. C. Taylor (editors).

Dioxane derivatives are judiciously prepared by reaction of a corresponding aldehyde (or a reactive derivative thereof) with a corresponding 1,3-diol (or a reactive derivative thereof), preferably in the presence of an inert solvent, such as benzene or toluene, and/or in the presence of a catalyst, for example strong acid such as sulfuric acid, benzene- or p-toluenesulfonic acid, at temperatures between about 20° C. and about 150° C., preferably between 80° C. and 120° C. Primarily suitable as reactive derivatives of the starting materials are acetals.

Some of said aldehydes and 1,3-diols and their reactive derivatives are known while some can be prepared without difficulty by standard methods of organic chemistry from compounds known from the literature. For example, the aldehydes are obtainable by oxidation of corresponding alcohols or by reduction of nitrites or corresponding carboxylic acids or derivatives thereof, and the diols by reduction of corresponding diesters.

Compounds in which an aromatic ring is substituted by at least one F atom can also be obtained from the corresponding diazonium salts by replacement of the diazonium group with a fluorine atom, for example by the methods of Balz and Schiemann.

As far as the linking of ring systems to one another is concerned, reference may be made, for example, to:
N. Miyaura, T. Yanagai and A. Suzuki in Synthetic Communications 11 (1981), 513–519; DE-C 39 30 663; M. J. Sharp, W. Cheng, V. Snieckus in Tetrahedron Letters 28 (1987) 5093; G. W. Gray in J. Chem. Soc. Perkin Trans. II 1989, 2041 and Mol. Cryst. Liq. Cryst. 172 (1989) 165, 204 (1991) 43 and 91; EP-A 0 449 015; WO-A 89/12039; WO-A 89/03821; EP-A 0 354 434 and EP-A 0 694 530 for the direct linking of aromatics and heteroaromatics; DE-A 32 01 721 for compounds with —$CH_2CH_2$— bridges, and Koji Seto et al. in Liquid Crystals 8 (1990) 861–870 for compounds containing —C—C— bridges.

Esters of the formula (I) can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols and phenols are known and can be prepared analogously to known processes.

Particularly suitable reactive derivatives of said carboxylic acids are the acid halides, especially the chlorides and bromides, and also the anhydrides, including mixed anhydrides, for example, azides or esters, especially alkyl esters having 1–4 carbon atoms in the alkyl group.

Particularly suitable reactive derivatives of said alcohols and phenols are the corresponding metal alcoholates or phenolates, preferably of an alkali metal, such as sodium or potassium.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoramide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula (I) are obtainable by etherification of corresponding hydroxy compounds, preferably corresponding phenols, where the hydroxy compound is judiciously first of all converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This product can then be reacted with the corresponding alkyl halide, alkylsulfonate or dialkyl sulfate, judiciously in an inert solvent, such as acetone, 1,2-dimethoxyethane, DMF or dimethyl sulfoxide, or else with an excess of aqueous or aqueous-alcoholic NaOH or KOH at temperatures of between about 20° and 100° C.

Regarding the synthesis of specific radicals $R^1$, reference may additionally be made, for example, to EP-A 0 355 008 for compounds with silicon-containing side chains and EP-A 0 292 954 and EP-A 0 398 155 for compounds with cyclopropyl groups in the side chain.

The provision of compounds of the formula (I) considerably broadens, in general terms, the palette of liquid-crystalline substances which from a variety of applications-related standpoints are suitable for the preparation of liquid-crystalline mixtures.

In this connection the compounds of the formula (I) possess a broad scope of application. Depending on the selection of the substituents they can be used as base materials forming the predominant part of liquid-crystalline phase compositions; or alternatively, compounds of the formula (I) can also be added to liquid-crystalline base materials from other classes of compounds in order, for example, to influence the dielectric and/or optical anisotropy of such a dielectric material and/or to optimize its threshold voltage and/or its viscosity.

The compounds of the formula (I) are particularly suitable for addition even in small amounts for influencing the dielectric anisotropy ($\Delta\epsilon$) toward higher negative values.

The invention also provides for the use of compounds of the formula (I) in liquid-crystal mixtures, preferably ferroelectric and nematic mixtures, especially ferroelectric mixtures.

The invention additionally provides liquid-crystal mixtures, preferably ferroelectric and nematic mixtures, especially ferroelectric mixtures, comprising one or more compounds of the formula (I).

The novel liquid-crystal mixtures generally contain from 2 to 35, preferably from 2 to 25 and, with particular preference, from 2 to 20 components.

They generally contain from 0.01 to 80% by weight, preferably from 0.1 to 60% by weight, particularly preferably from 0.1 to 30% by weight, of one or more, preferably from 1 to 10, particularly preferably from 1 to 5, very particularly preferably from 1 to 3, of the novel compounds of the formula (I).

Further components of liquid-crystal mixtures comprising novel compounds of the formula (I) are preferably selected from known compounds having smectic and/or nematic and/or cholesteric phases. These include, for example:

derivatives of phenylpyrimidine as described, for example, in WO 86/06401 and U.S. Pat. No. 4,874,542, meta-substituted aromatic compounds having a six-membered ring, as described, for example, in EP-A 0 578 054, silicon compounds as described, for example, in EP-A 0 355 008, mesogenic compounds having only one side chain, as described, for example in EP-A 0 541 081, hydroquinone derivatives as described, for example, EP-A 0 603 786, pyridylpyrimidines as described, for example, in WO 92/12974, phenylbenzoates as described, for example, in P. Keller, Ferroelectrics 1984, 58, 3 and J. W. Goodby et al., Liquid Crystals and Ordered Fluids, Vol. 4, New York 1984, and thiadiazoles as described, for example, in EP-A 0 309 514.

Examples of suitable chiral, nonracemic dopes are:

optically active phenylbenzoates as described, for example, in P. Keller, Ferroelectrics 1984, 58, 3 and J. W. Goodby et al., Liquid Crystals and Ordered Fluids, Vol.4, New York 1984, optically active oxirane ethers as described, for example, in EP-A 0 263 437 and WO-A 93/13093, optically active oxirane esters as described, for example, in EP-A 0 292 954, optically active dioxolane ethers as described, for example, in EP-A 0 351 746, optically active dioxolane esters as described, for example, in EP-A 0 361 272, optically active tetrahydrofuran-2-carboxylic esters as described, for example, in EP-A 0 355 561, and optically active 2-fluoroalkyl ethers as described, for example, in EP-A 0 237 007 and U.S. Pat. No. 5,051,506.

The mixtures can in turn be employed in electrooptical or fully optical elements, for example display elements, switching elements, light modulators, elements for image processing and/or signal processing or, generally, in the area of nonlinear optics.

Liquid-crystalline mixtures comprising compounds of the formula (I) are particularly suitable for use in electrooptical switching and display devices (displays). These displays are usually constructed in such a way that a liquid-crystal layer is enclosed on both sides by layers which are usually, in this sequence starting from the LC layer, at least one alignment layer, electrodes and a limiting sheet (for example of glass). In addition, they comprise spacers, adhesive frames, polarizers and—for color displays—thin color-filter layers. Other possible components are antireflection, passivation, compensation and barrier layers and electric nonlinear elements, such as thin-film transistors (TFTS) and metal-insulator-metal (MIM) elements. The structure of liquid-crystal displays has already been described in detail in relevant monographs (see, for example, E. Kaneko, "Liquid Crystal TV Displays: Principles and Applications of Liquid Crystal Displays", KTK Scientific Publishers 1987).

In addition the mixtures are suitable for field treatment, i.e. for operation in the quasi-bookshelf geometry (QBG) (see, for example, H. Rieger et al., SID 91 Digest (Anaheim) 1991, 396).

The novel mixtures are likewise suitable for use in ferroelectric liquid-crystal displays which are based on utilization of the DHF effect or the PSFLCD effect (pitch stabilized ferroelectric liquid crystal display, also termed SBF=short pitch bistable ferroelectric effect).

In addition, the compounds of the formula (I) can also be used as components of antiferroelectric liquid-crystal mixtures.

The contents of the publications mentioned in the description, especially regarding the synthesis of compounds of the formula (I), belong to the contents of this description by being cited.

The invention is illustrated in more detail by means of the examples, although this is not intended to represent a limitation.

EXAMPLE 1

9,9,10,10-Tetrafluoro-2,7-dihexyl-9,10-dihydrophenanthrene 4.1 g of 9,9,10,10-tetrafluoro-2,7-dibromo-9,10-dihydrophenanthrene are dissolved in 250 ml of THF and the solution is cooled to 0° C. 120 mg of 1,3-bis(diphenylphosphine)propanenickel(ll) chloride are added, and, at 0° C., 50 mmol of hexylmagnesium bromide in 100 ml of THF are added dropwise. Stirring is continued for 4 hours, and then for a further 18 hours at 50° C. The mixture is acidified with 1N HCl, the aqueous phase is saturated with NaCl and the phases are separated. The aqueous phase is subsequently subjected to extraction a number of times with tert-butyl methyl ether. The crude product is purified by chromatography on silica gel. This gives 3.45 g of 9,9,10,10-tetrafluoro-2,7-dihexyl-9,10-dihydrophenanthrene.

EXAMPLE 2

9,10-Difluoro-2,7-dihexylphenanthrene 3.8 g of 9,10-difluoro-2,7-dibromophenanthrene are dissolved in 250 ml of THF and the solution is cooled to 0° C. 120 mg of 1,3-bis(diphenyl-phosphine)propanenickel(ll) chloride are added, and, at 0° C., 50 mmol of hexylmagnesium bromide in 100 ml of THF are added dropwise. Stirring is continued for 4 hours, and then for a further 18 hours at 5° C. The mixture is acidified with 1N HCl, the aqueous phase is saturated with NaCl and the phases are separated. The aqueous phase is subsequently subjected to extraction a number of times with tert-butyl methyl ether. The crude product is purified by chromatography on silica gel. This gives 2.78 g of 9,10-difluoro-2,7-dihexylphenanthrene.

In analogy to Examples 1 and 2, 9,10-difluoro-2,7-dibromophenanthrene and 9,9,10,10-tetrafluoro-2,7-dibromo-9,10-dihydrophenanthrene can be reacted with other Grignard reagents to give symmetrically substituted compounds of the formula (Ia1) and (Ia2).

EXAMPLE 3

9,9,10,10-Tetrafluoro-2-bromo-7-octyl-9,10-dihydrophenanthrene

In analogy to Example 1, from 4.1 g of 9,9,10,10-tetrafluoro-2,7-dibromo-phenanthrene and 10 mmol of octylmagnesium bromide. The catalyst used is 0.2 mmol of 1,3-bis(diphenylphosphine)butanenickel(ll) chloride. Chromatography gives 2.4 g of 9,9,10,10-tetrafluoro-2-bromo-7-octyl-9,10-dihydrophenanthrene.

EXAMPLE 4

9,10-Difluoro-2-bromo-7-octylphenanthrene

In analogy to Example 2, from 4.1 g of 9,10-difluoro-2,7-dibromo-phenanthrene and 10 mmol of octylmagnesium bromide. The catalyst used is 0.2 mmol of 1,3-bis(diphenylphosphine)butanenickel(ll) chloride. Chromatography gives 2.1 g of 9,10-difluoro-2-bromo-7-octyl-phenanthrene.

In analogy to Example 3 and 4, 9,10-difluoro-2,7-dibromophenanthrene and 9,9,10,10-tetrafluoro-2,7-dibromo-9,10-dihydrophenanthrene can be reacted with other Grignard reagents to give monoalkyl-substituted compounds of the formula (Ia1) and (Ia2).

EXAMPLE 5

9,9,10,10-Tetrafluoro-2-hexyl-7-octyl-9,10-dihydrophenanthrene

In analogy to Example 1, from 9,9,10,10-tetrafluoro-2-bromo-7-octyl-9,10-dihydrophenanthrene and hexylmagnesium bromide. The catalyst used is 1,3-bis(diphenylphosphine)propanenickel(1 I) chloride. Chromatography gives 9,9,10,10-tetrafluoro-2-hexyl-7-octyl-9,10-dihydrophenanthrene

EXAMPLE 6

9,10-Difluoro-2-hexyl-7-octylphenanthrene

In analogy to Example 2, from 9,10-difluoro-2-bromo-7-octylphenanthrene and 10 mmol of hexylmagnesium bromide. The catalyst used is 0.2 mmol of 1,3-bis(diphenylphosphine)propanenickel(lI) chloride. Chromatography gives 9,10-difluoro-2-hexyl-7-octylphenanthrene.

In analogy to Example 5 and 6,9,10-difluoro-2-alkyl-7-bromophen-anthrenes and 9,9,10,10-tetrafluoro-2-alkyl-7-bromo-9,10-dihydro-phenanthrenes can be reacted with other Grignard reagents to give assymetrically substituted compounds of the formula (Ia1) and (Ia2).

EXAMPLE 7

2-(4-Decyloxyphenyl)-9,9,10,10-tetrafluoro-7-butyl-9,10-dihydrophenanthrene

From 9,9,10,10-tetrafluoro-2-bromo-7-butyldihydrophenanthrene and 4-decyloxyphenylboronic acid by means of palladium-catalyzed Suzuki coupling (in analogy to Acc. Chem. Res. 1982, 15, 178). The crude product is purified by column chromatography.

EXAMPLE 8

2-(4-Decyloxyphenyl)-9,10-difluoro-7-butyl-phenanthrene

From 9,10-difluoro-2-bromo-7-butylphenanthrene and 4-decyloxyphenyl-boronic acid by means of palladium-catalyzed Suzuki coupling (in analogy to Acc. Chem. Res. 1982, 15, 178). The crude product is purified by column chromatography.

EXAMPLE 9

2-Butoxy-5-(9,9,10,10-tetrafluoro-7-hexyl-9,10-dihydrophenanthrene-2-yl)pyridine From 9,9,10,10-tetrafluoro-2-bromo-7-hexyl-9,10-dihydrophenanthrene and 2-butoxypyridine-5-boronic acid in analogy to Example 7.

EXAMPLE 10

2-Butoxy-5-(9,10-difluoro-7-hexylphenanthrene-2-yl)pyridine

From 9,10-difluoro-2-bromo-7-hexylphenanthrene and 2-butoxypyridine-5-boronic acid in analogy to Example 8.

In analogy to Examples 7, 8, 9 and 10, 9,10-difluoro-2-alkyl-7-bromophenanthrenes, 9,10-difluoro-2-alkoxyl-7-bromophenanthrenes, 9,9,10,10-etrafluoro-2-alkyl-7-bromo-9,10-dihydrophenanthrenes and 9,9,10,10-tetrafluoro-2-alkyloxy-7-bromo-9,10-dihydrophenanthrenes can be reacted with further aryl- and heteroarylboronic acids to give asymmetrically substituted compounds.

We claim:

1. A fluorinated phenanthrene derivative of the formula (I)

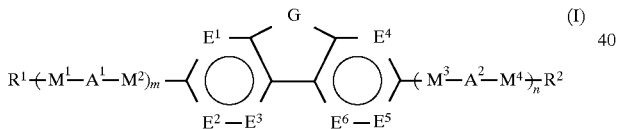

in which the symbols and indices have the following meanings:

$E^1$, $E^2$, $E^3$, $E^4$, $E^5$ and $E^6$ are identical or different and are —N—, —CF— or —CH—;

G is —$CF_2CF_2$— or —CF═CF—;

$R^1$, $R^2$ are identical or different and are hydrogen, —CN, —F, —Cl, —$CF_3$, —$CHF_2$, —$CH_2F$, —$OCF_3$, —$OCHF_2$, —$OCH_2F$ or a straight-chain or branched alkyl radical having 1 to 20 carbon atoms (with or without an asymmetric carbon atom), where alternatively one or more $CH_2$ groups can be replaced by —O—, —S—, —CO—O, —O—CO—, —O—CO—, —O—CO—O—, —CO—, —CS—, —CH═CH—, —C≡C—, cyclopropane-1,2-diyl, —Si($CH_3$)$_2$—, 1,4-phenylene, trans-1,4-cyclohexylene or trans-1,3-cyclopentylene, with the proviso that when either $R^1$ or $R^2$ is hydrogen the other cannot be, with the further proviso that oxygen atoms and/or sulfur atoms must not be attached directly to one another and/or where one or more hydrogen atoms of the alkyl radical can be substituted by —F—, —Cl, —Br, —$OR^3$, —SCN, —OCN or —$N_3$, or else are one of the following groups (optionally active or racemic);

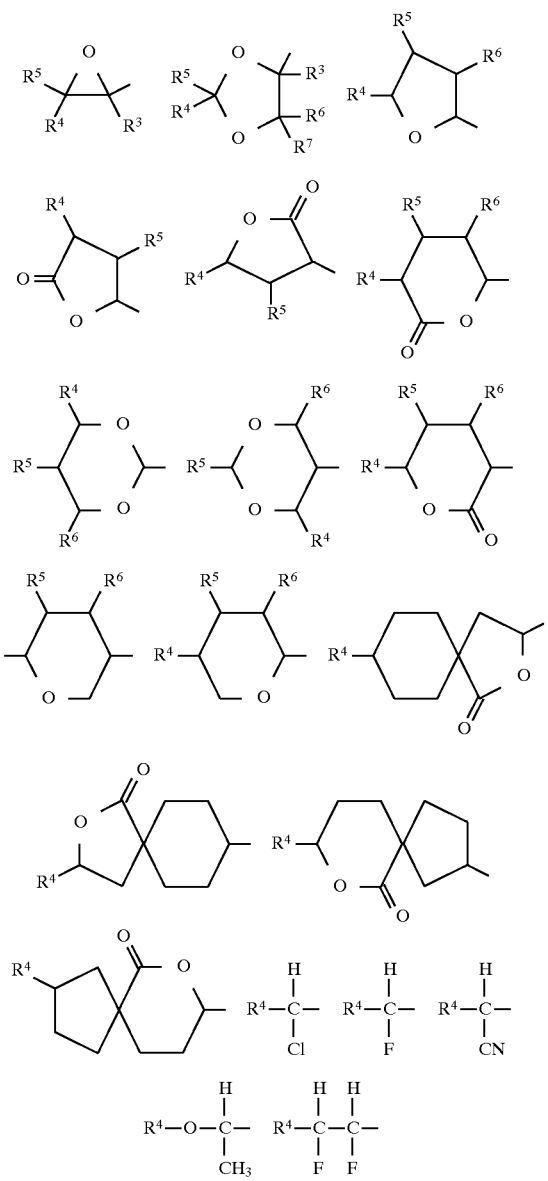

$R^3$, $R^4$, $R^5$, $R^6$, $R^7$ are identical or different and are hydrogen or a straight-chain or branched alkyl radical having 1–16 carbon atoms (with or without an asymmetric carbon atom), where alternatively one or more $CH_2$ groups can be replaced by —O— and/or —CH═CH—, with the proviso that oxygen atoms must not be attached directly to one another, and/or where one or more hydrogen atoms of the alkyl radical can be substituted by —F or —Cl; $R^4$ and $R^5$ can together also be —($CH_2$)$_4$— or —($CH_2$)$_5$— if they are attached to an oxirane, dioxolane, tetrahydrofuran, tetrahydropyran, butyrolactone or valerolactone system;

$M^1$, $M^2$, $M^3$, $M^4$ are identical or different and are —O—, —S—, —CO—, —CO—O—, —O—CO—, —O—CO—O—, —CO—S—, —S—CO—, —CS—O—, —O—CS—, —S—CS—S—, —O—CS—O—, —S—CO—S—, —CS—, —$CH_2$—O—, —O—$CH_2$—, —$CH_2$—S—, —S—$CH_2$—, —CH═CH—, —C≡C—, —$CH_2$—$CH_2$—CO—O—, —O—CO—$CH_2$—$CH_2$— or a single bond;

$A^1$, $A^2$ are identical or different and are 1,4-phenylene, where one or more hydrogen atoms can be replaced by F, Cl and/or CN, pyrazine-2,5-diyl, where one or two hydrogen atoms can be replaced by F, Cl and/or CN, pyridazine-3,6-diyl, where one or two hydrogen atoms can be replaced by F, Cl and/or CN, pyridine-2,5-diyl, where one or more hydrogen atoms can be replaced by F, Cl and/or CN, pyrimidine-2,5-diyl, where one or two hydrogen atoms can be replaced by F, Cl and/or CN, trans-1,4-cyclohexylene, where one or two hydrogen atoms can be replaced by CN and/or $CH_3$, 1,3,4-thiadiazole-2,5-diyl, 1,3-dioxane-2,5-diyl, 1,3-dithiane-2,5-diyl, 1,3-thiazole-2,4-diyl, where one hydrogen atom can be replaced by F, Cl and/or CN, 1,3-thiazole-2,5-diyl where one hydrogen atom can be replaced by F, Cl and/or CN, thiophene-2,4-diyl, where one hydrogen atom can be replaced by F, Cl and/or CN, thiophene-2,5-diyl where one or two hyrogen atoms can be replaced by F, Cl and/or CN, piperazine-1,4-diyl, piperazine-2,5-diyl, naphthalene-2,6-diyl, where one or more hydrogen atoms can be replaced by F, Cl and/or CN, bicyclo[2.2.2]octane-1,4-diyl, where one or more hydrogen atoms can be replaced by F, Cl and/or CN, or 1,3-dioxaborinane-2,5-diyl;

n, m are zero or one, but in total not more than 1.

2. A fluorinated phenanthrene derivative of formula (I) as claimed in claim 1, wherein $R^1$, $R^2$ are identical or different and are straight-chain or branched alkyl radicals (with or without an asymmetric carbon atom) having 1 to 16 carbon atoms, where alternatively one or more $CH_2$ groups can be replaced by —O—, cyclopropane-1,2-diyl or —$Si(CH_3)_2$—, with the proviso that oxygens must not be directly connected, and/or where one or more hydrogen atoms of the alkyl radical can be substituted by F; $R^1$ or $R^2$ can also be H, but not both simultaneously.

3. A fluorinated phenanthrene derivative of the formula (I) as claimed in claim 2, wherein $R^1$, $R^2$ are identical or different and are straight-chain or branched alkoxy radicals having 1 to 10 carbon atoms, where alternatively one $CH_2$ group, separated by at least two further $CH_2$ groups from the nucleus, can be replaced by —$Si(CH_3)_2$—.

4. A fluorinated phenanthrene derivative of formula (I) as claimed in claim 1, wherein the symbols $E^1$ and $E^4$ are identical or different and are —CF— or —CH— and $E^2$, $E^3$, $E^5$ and $E^6$ are —CH—.

5. A fluorinated phenanthrene derivative of formula (I) as claimed in claim 4, which has the formula:

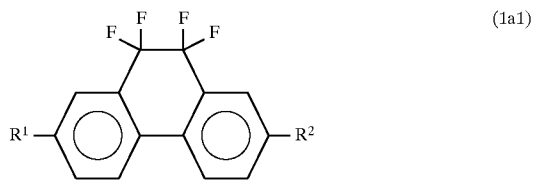
(1a1)

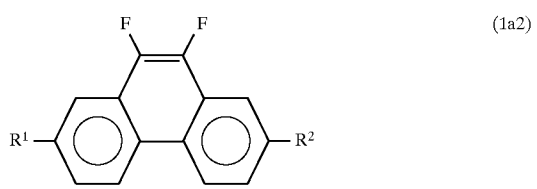
(1a2)

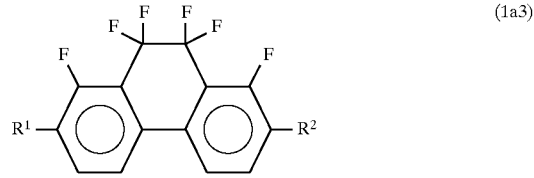
(1a3)

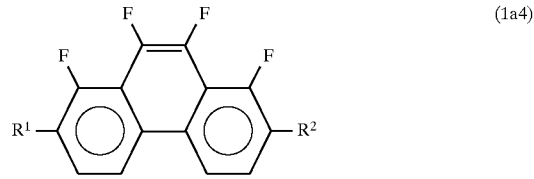
(1a4)

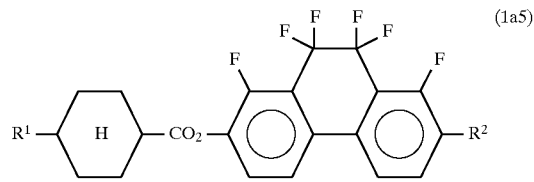
(1a5)

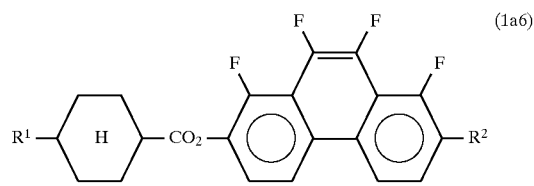
(1a6)

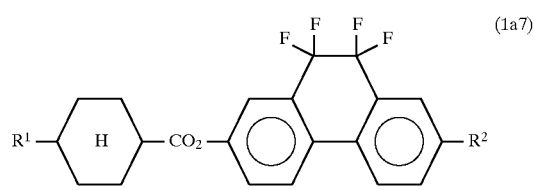
(1a7)

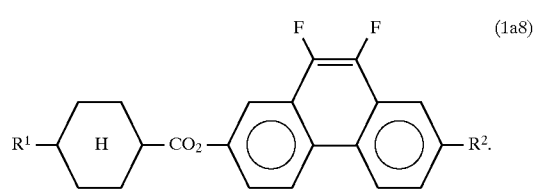
(1a8)

6. A liquid-crystal mixture comprising one or more compounds of the formula (I) as claimed in claim 1.

7. A liquid-crystal mixture as claimed in claim 6, which contains from 0.1 to 70 mol % of one or more compounds of the formula (I).

8. A liquid-crystal mixture as claimed in claim 6, which is ferroelectric.

9. A switching and/or display device comprising carrier plates, electrodes, at least one polarizer, at least one alignment layer and a liquid-crystalline medium, wherein the liquid-crystalline medium is a liquid-crystal mixture as claimed in claim 6.

* * * * *